(12) United States Patent
Garner et al.

(10) Patent No.: US 7,985,589 B2
(45) Date of Patent: Jul. 26, 2011

(54) QUANTIFICATION OF ANALYTES USING ACCELERATOR MASS SPECTROMETRY

(75) Inventors: Ronald Colin Garner, Sand Hutton (GB); Graham John Lappin, Harrogate (GB)

(73) Assignee: Xceleron, Limited, North Yorkshire (GB)

( * ) Notice: Subject to any disclaimer, the term of this patent is extended or adjusted under 35 U.S.C. 154(b) by 0 days.

(21) Appl. No.: 12/689,918

(22) Filed: Jan. 19, 2010

(65) Prior Publication Data
US 2010/0120156 A1    May 13, 2010

Related U.S. Application Data

(63) Continuation of application No. PCT/GB2008/002464, filed on Jul. 18, 2008.

(30) Foreign Application Priority Data

Jul. 19, 2007 (GB) .................................. 0714040.3

(51) Int. Cl.
*G01N 37/00*    (2006.01)
*G01N 33/48*    (2006.01)
*B01D 59/44*    (2006.01)

(52) U.S. Cl. ................... 436/8; 436/56; 436/57; 436/63; 436/161; 436/173; 436/174; 436/175; 436/177; 422/71; 250/281; 250/282; 250/303; 73/1.01; 73/1.02

(58) Field of Classification Search ................ 436/8, 56, 436/57, 63, 161, 173, 174, 175, 177; 422/68.1, 422/71; 250/281, 282, 302, 303; 73/1.01, 73/1.02

See application file for complete search history.

(56) References Cited

FOREIGN PATENT DOCUMENTS

| GB | 0714040.3 | * | 7/2007 |
| WO | WO95/04369 | | 2/1995 |
| WO | WO2004/077061 A1 | | 9/2004 |
| WO | WO2006/092584 A2 | | 9/2006 |
| WO | WO2008/064138 A2 | | 5/2008 |

OTHER PUBLICATIONS

Lappin et al. Analytical Biochemistry, vol. 378, No. 1, Jul. 1, 2008, pp. 93-95.*
Zoppi et al. Radiocarbon, vol. 49, No. 1, Apr. 2007, pp. 173-182.*
International Search Report for PCT/GB2008/002464, Oct. 24, 2008.
L.K. Fifield, *Rep Prog Phys* 62, (1999), p. 1223-1274.
R.C. Garner et al., *Drug Metab Dispos*, 30, (2002), p. 823-30.
R. C. Garner, *Curr Drug Metab*. 1, (2000), p. 205-213.
Lappin, G. & Garner, R.C., Chapter 11, *Ultra-sensitive detection of radiolabelled drugs and their metabolites using accelerator mass spectromety*, Handbook of Analytical Separations, Editor: I. Wilson,. 2003, Elsevier: Amsterdam. p. 331-349.
G. Lappin, et al., *Expert Opin. Drug Metab Toxicol*, 2, (2006), p. 419-427.
G. Lappin et al., *Clin Pharmacol Ther*, 80, (2006), p. 203-215.
G. Lappin, and S. Temple, *Accelerator Mass Spectrometry* in: *Radiotracers in Drug Development*, Taylor and Francis CRC Press, Florida, USA, (2006) p. 53-37.
G. Lappin et al., *Nat. Rev.*, 2, (2003), p. 233-240.
G. Laprin et al., *Expert Opin Drug Metab Toxicol*, 4, (2008), p. 1021-1033.
N. Sarapa et al., *J Clin Pharmacol*, 45 (2005), p. 1198-205.
J.S. Vogel, *Biotechniques*, 38, (2005), p. 25-9.
J.S. Vogel, *Radiocarbon*, 34, (1992), p. 344-350.
J.S. Vogel, and A.H. Love, *Quantitating Isotopic Molecular Labels with Accelerator Mass Spectrometry*: A.L. Burlingame, (Ed.), Methods in Enzymology, Academic Press, New York, (2005), p. 4020-422.
I.N. White, et al., *Trends in Pharmacol Sci.*, 25 (2004), p. 442-7.

* cited by examiner

*Primary Examiner* — Maureen M Wallenhorst
(74) *Attorney, Agent, or Firm* — Prout International IP, LLC

(57) ABSTRACT

The invention provides a calibrating method for use in a method of determining the quantity of an analyte labeled with an accelerator mass spectrometry (AMS) isotope in a test sample. The samples can include, for example, urine, faeces, plasma or blood. The analyte can be, for example, a drug or metabolite of a drug.

24 Claims, 2 Drawing Sheets

US 7,985,589 B2

QUANTIFICATION OF ANALYTES USING ACCELERATOR MASS SPECTROMETRY

This application is a continuation of International Application No. PCT/GB2008/002464, filed on Jul. 18, 2008, which claims priority to Great Britain Application No. 0714040.3, filed Jul. 19, 2007, the disclosures of all of which are incorporated by reference in their entirety.

This invention relates to a method for improving upon the accuracy with which the quantity of certain isotopically labelled analytes may be determined in a sample of interest. More particularly the invention allows internal standardisation when quantifying analytes using Accelerator Mass Spectrometry (AMS).

INTRODUCTION

Bioanalysis, typically conducted using Liquid-Chromatography Mass-Spectrometry (LC-MS), is routinely performed during clinical studies (phase I, II and III) and sometimes on animal samples from toxicology studies.

In LC-MS, analytes are separated using conventional HPLC methods and the eluant from the HPLC passed into the ion source of a mass spectrometer. Here the analytes are ionized by one of a variety of ionization techniques (e.g. electrospray or atmospheric pressure ionization (API)). Depending upon the energy of the ionization, some molecular fragmentation of the analyte may occur. The ions, either positively or negatively charged, are extracted from the ion source by virtue of their charge. These are separated in magnetic or quadrupole fields according to the mass of the ion (m) divided by the charge (z). In most cases, particularly with small molecules, z=1 such that the resultant mass spectrum reveals the molecular weight of the analyte. Depending upon the type of ionization employed, positive ions are often formed by the addition of $H^+$, and therefore the ion representing the molecular weight (i.e. the molecular ion) is depicted as $[M+1]^+$. The opposite can also happen: negative ions are formed by the extraction of $H^+$ and hence the molecular ion is depicted as $[M-1]^-$.

Some instruments have two mass spectrometers in series, separated by a gas collision cell. These are known as tandem mass spectrometers. Where the mass spectrometers are quadrupoles, they are known as triple quadrupole mass spectrometers. Ions enter the collision cell from the first mass spectrometer (parent ions) and are fragmented, the fragments being detected with the second mass spectrometer (daughter ions). This is known as LC-MS/MS.

Mass spectra show the absolute molecular weights of the ions. For example, the average molecular weight of 2-hydroxy-2-pyrrole-quinoline, taking the abundance of each isotope of carbon, hydrogen, nitrogen and oxygen into account is 210.24. The mass spectrometer, however, detects the abundance of each individual isotope. For 2-hydroxy-2-pyrrole-quinoline, the isotope abundance of carbon predominates and therefore the $[M+1]^+$, m/z 211 ion, is based on $^{12}C$. The ion at m/z 212 is based on $^{13}C$ and the ion at m/z 213 is based on $^{14}C$. The natural abundance of $^{14}C$ is very small: $7.4 \times 10^{11}$ carbon atoms typically include just 1 $^{14}C$ atom.

Bioanalysis is generally carried out on a very large scale and, notwithstanding the foregoing discussion, does not typically involve the detection and quantification of radiolabelled drugs.

In bioanalysis, samples are typically analysed for a target molecule—for example a parent drug (e.g. the molecule administered to a human, animal or other biological system) and sometimes a number of specific metabolites. For brevity references herein to a "target molecule" are to be understood to refer to the molecule of interest which is the subject of analysis and may be, for example, a potential or putative drug candidate or a metabolite thereof. Bioanalysis results are used to generate pharmacokinetic data from large numbers of human subjects participating in the clinical trials.

In bioanalysis using LC-MS, a biological sample is extracted (e.g. by solvent extraction of plasma) and the resultant extract submitted to LC-MS where the target molecule is detected and quantified. Quantification in this way, however, is complicated by the following:

1. Extraction of the target molecule from, for example, plasma may not be complete and an unknown amount may be left unextracted. This may, moreover, vary from sample to sample and extraction can be concentration-dependent.
2. Losses may occur during separation on HPLC (prior to MS analysis). In other words the HPLC column recovery may not be 100%. Similarly to 1, above column recovery may vary from sample to sample and be concentration-dependent.
3. Mass spectrometers ionise compounds prior to detection. The process of ionisation is very compound-dependent and the ionisation efficiency can change over time. Accordingly, it is not possible to quantify by mass spectrometry without reference to a standard.

In order to compensate for these deficiencies quantification of target molecules is generally subject to calibration. In order to do this, two substances are typically required in highly pure states: (1) the target molecule itself as a reference standard; and (2) a compound with a chemical structure very similar to that of the target molecule, which is used as an internal standard. The ideal internal standard is generally considered to be deuterated target molecule, since these have a very similar chromatographic retention time to the non-deuterated target molecule but may be distinguished in LC-MS by virtue of their higher molecular weight during the mass spectrometry step. However, deuterated standards are not always available. If a deuterated internal standard is unavailable a compound structurally different to the target molecule (i.e. an analogue) can be used but this should be as structurally similar to the target molecule as possible.

In order to calibrate, control matrix (e.g. plasma) is typically taken from donors (e.g. humans) that have never been exposed to the target molecule of interest. A different concentration of the reference standard target molecule is added to each of a series of such control plasma samples (for example eight samples may comprise 10, 20, 50, 100, 500, 1000, 1500 and 2000 pg/mL or, to give another example, 100, 150, 200, 250, 500, 1000, 1500 and 2000 pg/mL of the reference target molecule). In addition, a known and equal amount of internal standard is added to each control plasma sample (for example 500 pg/mL internal standard).

Each sample so prepared is analysed by a suitable chromatographic method (e.g. LC-MS) and the amounts for target molecule and internal standard determined. The data obtained may be used to construct a calibration graph or line in which, for example, the target molecule concentration (known from the amounts initially added to the control plasma samples) can be plotted on the x-axis and the ratio of the amount of isolated target molecule to that of the internal standard (these amounts being determined by LCMS) can be plotted on the y-axis. It is important to note here that such plots are not necessarily linear.

In order to then quantify unknown concentrations of target molecule present in real samples obtained from clinical or other trials, an exact and known amount of internal standard is added to each such sample. The sample is extracted and analysed by LC-MS to determine the amounts of target molecule and the internal standard. The ratio of these amounts may be used to derive the corresponding target molecule concentration by comparison of the ratio (analyte:internal standard) with the target molecule concentration to which it corresponds on the calibration graph/line.

If any loss of target molecule occurs during sample preparation or elsewhere, then this is corrected for by proportionate losses of the internal standard allowed for by the ratiometric nature of the calibration. Likewise, if the LCMS technique leads to losses or other failed or lessened detection of target molecule, these losses should be mirrored by corresponding losses of internal standard. Thus the calibration line truly characterises the method, analytical losses and the response of the mass spectrometer.

In addition to the routine bioanalyses discussed above, related experiments can also be conducted with radiolabelled drugs, typically labelled with $^{14}C$. Such experiments are not generally conducted with the large number of samples associated with clinical trials but tend to be distinct experiments, designed to examine the metabolism and pharmacokinetics of the drug. In such studies, LC-MS is generally not used to quantify the drug concentration; instead the target molecule is typically quantified by determining the levels of radioactivity using radiotracer techniques. The reason for this is essentially that the target drug (or perhaps a particular metabolite) in such studies in generally known and can be isolated with ease. Thus identification is less of the challenge; all that needs to be done in quantification. If a particular target molecule, such as parent drug, is quantified using radiotracer techniques, however, then although the target molecule will be available in both the non-radiolabelled and $^{14}C$-labelled forms, it is unlikely that an appropriate $^{14}C$-internal standard will be available. For this reason, target molecule quantification employing radiotracers has traditionally been performed using an absolute method of analysis. This entails measurement of the amount of radioactivity in a HPLC eluate and the result deemed to equate directly to the concentration of the target molecule in the original matrix.

The use of a radioactive tracer has the advantage that measurement of the radioactivity is directly related to the amount of target molecule present. Unlike LC-MS there is no ionisation efficiency factor to consider. Nevertheless, the uncertainties associated with sample extraction and possible losses on the chromatography column still apply (i.e. items 1 and 2 discussed above). For this reason the deeming of the radioactivity measured to equate directly to the target molecule concentration in the original matrix is, put bluntly, no more than a convenient assumption.

In addition radiotracer techniques such as liquid scintillation (LSC) suffer from an innate insensitivity. For LSC determination of $^{14}C$, for example, the sample is first dissolved in a liquid scintillation cocktail. Energy from the β-radiation, emitted from $^{14}C$ during a decay event, excites the liquid scintillant. Upon returning to the energetic ground state, the scintillant emits photons of light, which are detected by a photomultiplier tube. The number of photons emitted by the scintillant is therefore in proportion to the number of radioactive decay events. However, since the half-life of $^{14}C$ is 5760 years, relatively few of the $^{14}C$ atoms in a sample are decaying at any one time. In fact, it takes over a billion atoms of $^{14}C$ to generate an average of only one disintegration per minute (dpm).

As an alternative to the use of radiotracer techniques, AMS may also be used to directly quantify the amount of a target molecule present in a sample.

AMS is a technique for determining the quantity of certain isotopes. It was invented in the 1970's for archaeological carbon dating and was first applied to pharmaceutical research in the 1990s (Garner, R. C. (2000) Accelerator mass spectrometry in pharmaceutical research and development—a new ultrasensitive analytical method for isotope measurement. *Curr Drug Metab.* 1(2) 205-213).

Unlike LSC, AMS is an extremely sensitive method of analysis requiring just 1,000 atoms to reach the detector (Lappin, G. & Garner, R. C., *Ultra-sensitive detection of radiolabelled drugs and their metabolites using accelerator mass spectrometry, in Handbook of Analytical Separations*, I. Wilson, Editor. 2003, Elsevier: Amsterdam. p. 331-349). Since AMS is an isotope ratio technique, the substance under analysis has to be enriched with a rare isotope. Whilst other isotopes may be used, in biomedical research this isotope is very commonly $^{14}C$ (in which case the $^{12}C:^{14}C$ isotope ratio may be measured).

AMS has many applications in biomedical and other research but its relevance to the present discussion is its utility in measuring very low concentrations of compound present in a given matrix. One of the most significant advantages of AMS is that it can detect and quantify, in relatively short analytical times, levels of radioactivity that are so low that the dose needed to be administered to a human subject falls below the stipulated level of radioactivity which requires regulatory approval. Typically the compound analysed is a drug substance, or a metabolite thereof, and the matrix is a biological sample, i.e. one obtained from a human or animal subject, for example plasma. However the compound analysed may be any compound in any matrix (e.g. an environmental pollutant in soil).

As discussed above, a common method of measuring the concentration of a target molecule in a matrix is LC-MS. In biomedical research, LC-MS can typically measure 100 pg of compound per mL sample. At the time of writing (2007) LC-MS can achieve better sensitivity (e.g. 10 pg/mL). AMS, however, can routinely achieve a sensitivity of 1 pg/mL and, with some routine method optimisation readily achievable by those skilled in the art, the sensitivity can reach the femtogram or attogram range ($10^{-15}$-$10^{-18}$ g).

AMS has therefore been used as an analytical tool in biomedical research where greater sensitivity of analysis is required. The compound under analysis contains an enriched amount of an AMS isotope, typically $^{14}C$, and AMS measures the isotope ratio of the compound in order to determine its concentration. Whilst LC-MS does not require the compound to have an isotopic enrichment its sensitivity does not reach the levels attainable with AMS.

Typically, in AMS analysis, the compound to be analysed is first extracted from the matrix in which it is found before isolation by HPLC. The HPLC eluant is collected as a series of fraction(s) and those corresponding to the compound of interest are aliquoted for analysis by AMS. At the time of writing (2007), notwithstanding the details in WO95/04369, there is not believed to be any routine interface that effectively routinely couples the separation step (e.g. by HPLC) to AMS.

This method assumes there are no analytical losses in the extraction and isolation processes. By extraction is meant an initial purification step or steps of the compound to be analysed from the matrix in which it is found (e.g. separation of the compound to be analysed and other compounds from the proteinaceous materials found in blood). Isolation refers to a further purification step or steps, typically to purify the compound to be analysed by separation from all remaining components from the matrix present after the extraction step(s). Depending upon their specific properties, however, some compounds may exhibit significant amounts of binding and so losses can occur during extraction and HPLC analysis. The result from conventional AMS analysis can therefore give results significantly lower than the true value. This is particularly problematic when it is desired to analyse very small amounts of compound by AMS due to binding effects and experimental losses during extraction and purification for example. As a result the inherent ability of AMS to detect small quantities of AMS isotopically labelled target molecules may be considered to be associated with increasing errors when quantifying small amounts of material.

The present invention is intended to ameliorate one or more of the above-mentioned problems in the art.

SUMMARY OF THE INVENTION

We have developed a methodology to address the uncertainties and errors caused by binding and experimental losses preparatory to analysis of samples by AMS. It exploits the fact that compounds for AMS analysis are enriched with AMS isotopes, e.g. $^{14}C$.

The present invention relates to a method of internal standardisation when quantifying an AMS isotopically labelled analyte (hereinafter "analyte") using AMS. An analyte is thus the AMS isotopically labelled compound that it is wished to quantify and may be any compound of interest labelled with an AMS isotope. The invention employs an internal standardisation methodology analogous to that applied in bioanalysis described above but with the fundamental difference that a compound structurally identical to the analyte, but which is not labelled with an AMS isotope (hereinafter the "counterpart analyte") is used as an internal standard.

Viewed from one aspect, therefore, the invention provides a calibrating method for use in a method of determining the quantity of an analyte labelled with an AMS isotope in a test sample, said calibrating method comprising:
 (i) contacting a plurality of samples contaminated with neither said analyte nor a non-labelled counterpart analyte with a known quantity of said counterpart analyte and a quantity C of analyte to afford a plurality of calibrating samples, wherein each of said calibrating samples contains a known quantity of counterpart analyte but a different quantity C;
 (ii) measuring by AMS the quantity C of analyte added to each of the plurality of samples;
 (iii) separating the analyte and counterpart analyte from other species in the plurality of samples to afford a plurality of purified samples;
 (iv) measuring a quantity A of analyte in said purified samples by AMS; and
 (v) measuring a quantity B of counterpart analyte in said purified samples.

When measuring the quantity B of counterpart analyte in said purified samples, this measuring may be only of counterpart analyte. Alternatively, the measuring may be of both counterpart analyte and analyte if the measuring technique cannot distinguish between counterpart analyte and analyte. In the latter case, discussed in greater detail below, such measuring may be considered to be only of the counterpart analyte if it is present in sufficient excess to the analyte.

The data obtained from the method according to the first aspect of this invention may be used to relate the absolute amount of analyte C present in said samples prior to submission to the method, as determined by AMS, to the ratio A:B. Thus, if this ratio is determined under similar conditions to those practised in the method above for a test sample in which the amount of analyte is unknown, but in which a known amount of counterpart analyte is present, the amount of analyte present in the test sample may be determined with reference to the data obtained from the method according to the first aspect of this invention. This forms a further aspect to the invention.

Viewed from this aspect the invention provides a method for use in determining the quantity of an analyte labelled with an AMS isotope in a test sample, said method comprising:
 (i) contacting said test sample with a known quantity of a non-labelled counterpart analyte;
 (ii) separating the analyte, if present, and counterpart analyte from other species in the test sample to afford a purified test sample;
 (iii) measuring a quantity A of analyte in said purified test sample by AMS; and
 (iv) measuring a quantity B of counterpart analyte in said purified test sample.

Similarly to the practise of the first aspect of the invention, when measuring the quantity B of the counterpart analyte in the purified test sample, this measuring may be only of counterpart analyte. Alternatively, the measuring may be of both counterpart analyte and analyte if the measuring technique cannot distinguish between counterpart analyte and analyte. In the latter case, and is discussed in greater detail below, such measuring may be considered to be only of the counterpart analyte if it is present in sufficient excess to analyte.

By comparing the ratio A:B from the purified test sample with the data obtained from practising the first aspect of the invention correlating A:B ratios with known C values, the unknown quantity of analyte in the test sample submitted to the method of the second aspect of the invention may be determined.

DETAILED DESCRIPTION OF THE INVENTION

Figure 1:
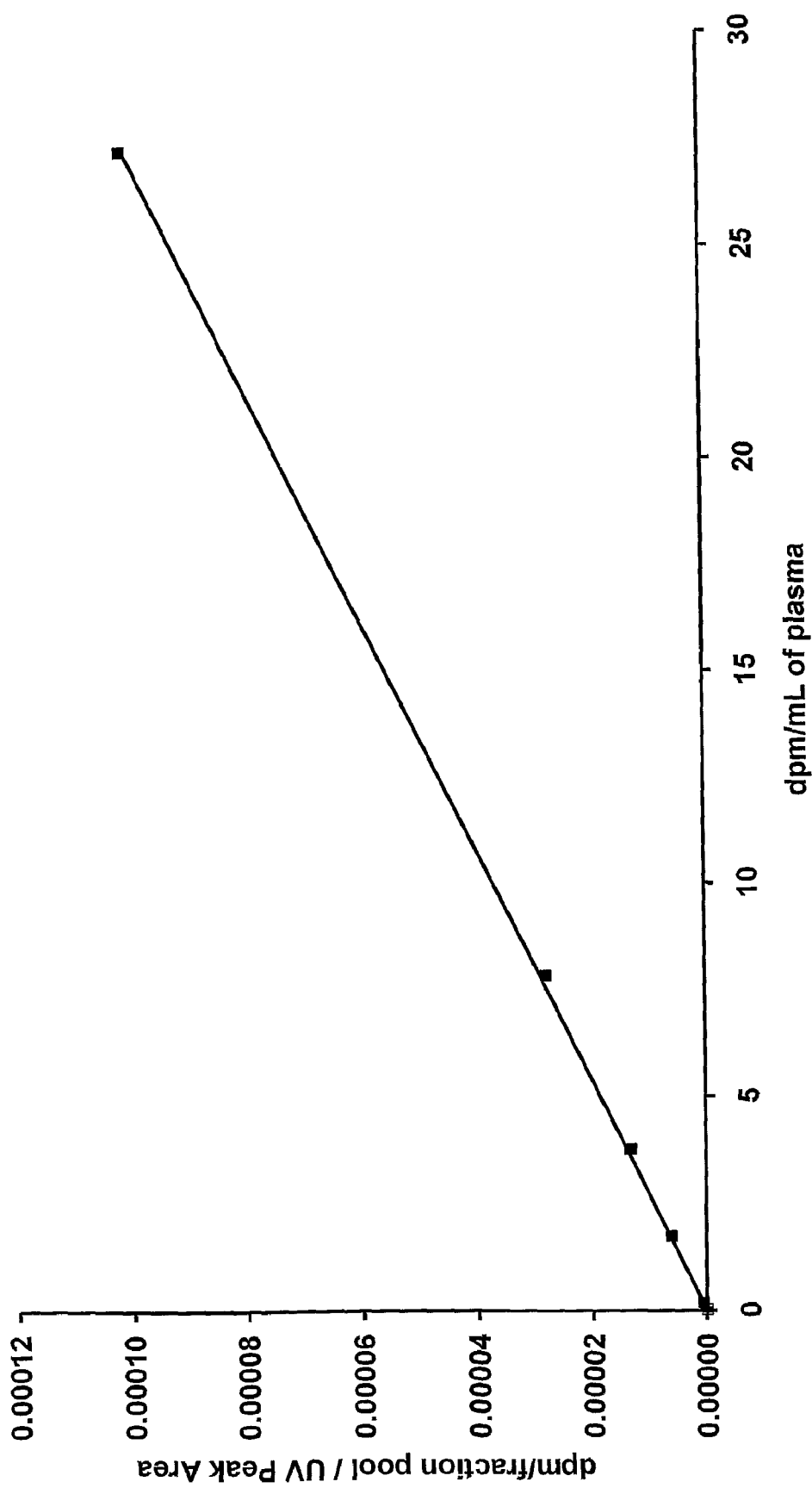
FIG. 1 shows a calibration curve obtained by plotting a ratio of B:A against C for data obtained from practice of a calibratory method of the invention.

The invention is distinct from bioanalysis as described hereinbefore. For example, it is a requirement of the invention that AMS isotopically labelled analytes are involved. Secondly, in bioanalysis the internal standard has to be as closely related structurally to the analyte as possible. In the method described here the internal standard is the non-labelled counterpart to the labelled analyte. This approach is possible because the analyte is distinguishable from the internal standard by the presence of an AMS isotope. Two methods of analysis are used: the quantity of analyte is determined by AMS and the quantity of counterpart analyte is determined by a different analytical method.

The following discussion frequently focuses upon the use of the methods of the invention in the determination of $^{14}C$-labelled analytes, and in particular in the analysis of clinical samples, e.g. obtained from clinical trials although it is to be understood that the invention is not to be considered to be so limited.

Where the sample is a clinical sample, this may be taken at a specified time after administration of analyte during a clinical trial. In addition, the clinical sample(s) may also include, if this is desired, pre-dose samples of matrix.

It is also appreciated that there is focus herein on the use of HPLC in effecting separating according to the methods of this invention. However, it will be understood that the invention is not considered to be so limited. Any method of separation (by HPLC or otherwise) may be used according to the practice of the methods of this invention providing it serves to isolate the analyte of interest from other labelled compounds such that AMS analysis of the resultant purified test sample allows accurate quantification of the amount of analyte in the purified test sample. This may include a method of separation which permits direct interfacing with the AMS machine, such as described in WO95/04369. Typically, however, the separating and AMS measuring steps are not interfaced.

The following definition are used herein:

In the context of clinical trials of potential drug candidates, for example, the analyte may be the parent drug under test in such a clinical trial, or a metabolite of the parent drug. The analyte will generally be a $^{14}$C-labelled compound and the discussion herein focuses upon such $^{14}$C-labelled compounds. However, given the ability to detect minute quantities of other AMS isotopes, the analyte may be any compound labelled with an AMS isotope.

All atoms have isotopic forms, some of which are suited to AMS analysis. For example a biological labelled with $^{129}$I is useful for AMS detection whereas a biological labelled with $^{131}$I, although highly active is probably of limited use in humans due to safety issues. Similarly a biological labelled with $^{14}$C is useful for AMS detection whereas a biological labelled with $^{13}$C is of widespread use in many other non-radioactive techniques, such as NMR detection but is of no use in AMS analysis. Particularly unsuitable isotopes, notably nitrogen, fail to form negative ions.

An AMS isotope may be any isotope that is susceptible to AMS analysis. AMS isotopes preferably have very low natural abundances, for example an isotopic abundance in the range of from $1\times10^{-3}$% to $1\times10^{-15}$%, e.g. $1\times10^{-5}$% to $1\times10^{-15}$%. The sensitivity of AMS relies on the fact that AMS isotopes have such low natural backgrounds, such as approximately $1.4\times10^{-1}$% for $^{14}$C. (The background for $^{13}$C is 1.1%, which by comparison is huge). Preferably AMS isotopes have long half lives or could be stable isotopes provided they have low natural abundances, for example within the ranges discussed hereinbefore in excess of weeks, for example greater than 30 days, or greater than 60 days, and up to thousands of years for ease of handling.

An AMS isotope may be selected from AMS isotopes of hydrogen, beryllium, carbon, aluminium, phosphorus, chlorine, calcium, manganese, iron, selenium, iodine, barium and lanthanides and actinides such as uranium or plutonium, in particular isotopes selected from the group comprising $^3$H, $^7$Be, $^{10}$Be, $^{14}$C, $^{17}$O, $^{18}$O, $^{26}$Mg, $^{26}$Al, $^{32}$Si, $^{35}$S, $^{36}$Cl, $^{41}$Ca, $^{55}$Fe, $^{60}$Fe, $^{53}$Mn, $^{79}$Se, $^{59}$Ni, and $^{129}$I. More commonly the isotope is selected from one or more of $^3$H and $^{14}$C. Most commonly the isotope is $^{14}$C.

Whilst emphasis is placed upon the use of $^{14}$C herein as the most commonly used AMS isotope, it will be appreciated that this is in part because the vast majority of drugs are organic. Other isotopes have been or could be used, however, including those AMS isotopes discussed hereinbefore.

The internal standard (the "counterpart analyte") used in the methods of the present invention is a compound identical to the analyte except that it does not contain the AMS isotope present in the analyte.

Control matrix refers to a sample used according to the first aspect of this invention, i.e. sample uncontaminated with the analyte, or counterpart analyte. In the context of clinical trials a control matrix may therefore be commercially obtained plasma, pre-clinical samples, or samples from subjects not participating in the clinical trial. Typically control matrix will be serum, or plasma, obtainable from blood. However, it will be understood that it may be desired to analyse other matrices such as urine, faeces or tissue.

In contrast to "control matrix", "matrix" is used herein to refer to a test sample that it is desired to analyse to determine an amount of analyte. Matrices may therefore be selected from the same group of materials as control matrices.

"Calibrating extraction solvent" refers to a solvent comprising the counterpart analyte at a concentration to achieve a particular amount when a control matrix extract is analysed by HPLC, together with $^{14}$C-containing (or other AMS labelled) analyte at a given concentration. Typically, the calibrating extraction solvent is acetonitrile although other solvents, e.g. methanol, may be used as is known by the skilled person. A calibrating extraction solvent is generally used as part of the separating step according to the method of the first aspect of the invention.

A "standard extraction solvent" is generally used as part of the separating step according to the method of the second aspect of the invention. Like the calibrating extraction solvent, the standard extraction solvent is typically acetonitrile although other solvents, such as e.g. methanol, may be used, as well as other methods such as solid phase extraction, as known to the skilled person. The standard extraction solvent typically comprises the counterpart analyte at a concentration to achieve a particular amount when the extract is injected into the HPLC. In contrast to the calibrating extraction solvent, the standard extraction solvent contains no analyte.

The test samples, which may be analysed for analyte according to this invention, may originate from any source. Typically these samples will originate from humans or animals, in particular humans. For example, these may arise from human microdosing or absolute bioavailability studies, in particular in humans.

Human microdosing, sometimes referred to as Human Phase 0 clinical trials, is a relatively new concept, which relies on the ultrasensitivity of AMS. Through human microdosing, it is possible to conduct detailed human metabolism studies after administration of as little as 0.5 µg of drug substance. More typically, however, 100 µg of drug are administered (a microdose is defined by both the EMEA and FDA as 100th of the predicted pharmacological dose but never to exceed 100 µg). In microdosing one or more drug candidates are taken into humans at trace doses in order to obtain early ADME (absorption, distribution, metabolism and excretion) and PK (pharmacokinetic) information. This information may then be used as part of the decision tree to select which of the microdosed drugs has the appropriate PK parameters to take further. The aim of these low dose screening ADME studies is to try to ensure fewer drugs have to be dropped later down the development pathway because of inappropriate metabolism (e.g. first pass, too short a half-life, poor bioavailability etc). As many as one drug in three will be dropped at the Phase 1 stage of drug development because of PK, pharmacodynamic or toxicity issues. Human microdosing aims to reduce attrition at Phase 1.

In the microdosing approach a potential drug candidate can be administered to human volunteers at doses from as little as 1 µg to up to 100 µg. Blood, urine or faecal samples are collected over time and the resultant samples analysed for $^{14}$C or other AMS isotope content by AMS to determine ADME and PK data.

Absolute bioavailability, as is known in the art (see for example G. Lappin, M Rowland and R C Garner, *Expert Opin. Drug Metab Toxicol* (2006) 2(3):419-427) involves the intravenous administration of a compound (typically a drug candidate). Such studies are generally difficult to conduct because problems relating to solubility, analytical sensitivity and the fact that IV toxicology data are normally required to support the study. However these problems may be addressed by using microdoses of AMS isotopically labelled compounds.

In microdosing and absolute bioavailability studies the analyte is administered to subjects alongside the counterpart analyte, the latter of which, being non-labelled, is normally a potential drug candidate. Typically, the mixture will be only 'lightly labelled'. By lightly labelled is meant that the amount of radioactivity is very low, typically being only 200 nCi to a human subject (approximately twice the amount of radioactivity due to $^{14}C$ already in the body).

It is stressed here that the terms analyte and counterpart analyte are being used to distinguish the AMS isotopically labelled compound from the corresponding (counterpart) compound which is not labelled. In practice the analyte will generally be found with, and thus administered alongside, the counterpart analyte.

When transported within the body of the subject (e.g. human subject) to which the microdose (for example) is administered, a 100 µg dosage (i.e. including analyte and counterpart analyte) reaches a maximum concentration of approximately 500 pg/ml. Typically the amount of counterpart analyte added as internal standard to such samples might be 5 µg/ml. This means that the amount of internal standard is at least 10,000 times higher than the amount of counterpart analyte originally present in the test sample arising from administration to the subject. It is this reasonable to deem the internal standard added to the such test samples to be the only source of counterpart analyte measured in the purified test samples. Typically the amount of counterpart analyte present as internal standard will be at least 98 wt % or more typically 99 wt % or more, more typically still 99.9 wt % or more or 99.95 wt % or more of all counterpart analyte present is a given purified test sample.

The invention relies on distinguishing between two structurally identical chemical entities (analyte and internal standard) and the practise of two methods of quantification, one of which is AMS for the analyte, the other, for counterpart analyte, being for example UV absorption, fluorescence or any other detection method useful in (generally) chromatographic detection, including mass spectrometry.

As discussed above the present invention is particularly well-suited to the measurement of low concentrations of analyte. In situations typical with AMS analysis, the levels of analyte in the sample can be extremely small (e.g. $10^{-18}$ to $10^{-9}$ g). Handling such small amounts of material is particularly difficult. As an illustration, no more than that, assume that a surface (e.g. the inside of a sample tube) has a few active binding sites and can adsorb up to 100 fg ($10^{-13}$ g) of material. With LC-MS a typical limit of detection (LOD) is around 100 pg, which is 1,000 times higher than losses due to binding (i.e. 0.1%) which may be considered to be negligible. At lower concentrations, however, the amount lost due to binding is proportionately higher. If the concentration was 1 pg/mL, then the binding of 100 fg would result in a 10% loss of analyte, which is significant. According to the present invention, however, the analyte present in the test sample is labelled, typically with $^{14}C$, and counterpart analyte is added to this test sample as an internal standard. Advantageously, this has the effect of raising the sum of the concentrations of analyte and counterpart analyte from, say, the 1 fg/mL level to the 200 pg/mL level (a million-fold higher), thus ameliorating or obviating the problems associated with the analysis of very small amounts of sample.

Before practising the calibrating method of the invention, it is typical to undertake some preliminary investigations. These include confirming by AMS that all samples of counterpart analyte are devoid of the AMS isotope present in the analyte, that is to say that they contain normal, background levels of that isotope at a maximum.

Similarly, the development of a suitable separating protocol in order to isolate the analyte and counterpart analyte from the other compounds (for example putative metabolites) that could interfere in the quantification of analyte and counterpart analyte is not within the ambit of the present invention and is not discussed here. However, the development of an appropriate separating protocol is within the skill of the skilled person. As mentioned already, the separating modality used accordance with the methods of this invention may be electrophoresin or may be a chromatographic method such as high performance liquid chromatography (HPLC), gas chromatography (GC) or thin-layer chromatography (TLC). Typically HPLC is used.

Likewise, determination of the solubility and stability of an analyte in any given solvent is not within the ambit of the present invention. It will be appreciated that the solubility and stability will vary from analyte to analyte and may be determined by the skilled person. In this regard, it will be understood that the solvent used to extract the counterpart analyte and analyte and from the sample will be determined to a certain extent by the solubility and stability of the analyte which it is desired to quantify according to this invention.

Where UV absorbance is used to detect the presence of the analyte in the separating modality used according to the present invention the $\lambda_{max}$ is initially determined. Generally, where HPLC is used, UV absorbance is a typical and convenient detection method for the counterpart analyte. However, it will be appreciated by the skilled person that other methods of detection could be used.

Where UV response is used in order to detect the counterpart analyte on HPLC, the reproducibility of the HPLC-UV response is typically confirmed by using 3 or more injections, with at least one preferably carried out on a separate day. Notwithstanding this, the precise means by which reproducibility is confirmed will depend on the specific characteristics of the analyte of interest. Similarly, the extent of any chromatographic carry-over is assessed in a similar way.

Furthermore, prior to practising this invention, the skilled person will generally, in developing an appropriate HPLC assay for the separating system, determine what amount of counterpart analyte, injected onto the HPLC column, will give an appropriate signal to noise ratio, without adversely affecting the peak shape (for example due to overload of the column) and is soluble at the concentration used. This amount is referred to herein as the 'standard quantity', that is the amount of counterpart analyte injected onto the HPLC column to be used for quantification by UV detection.

After determination of the standard quantity, the concentration of a standard solution of counterpart analyte may be calculated such that, for example, x µl of a standard counterpart analyte spiked into y µl of matrix followed by z µl injected onto the HPLC will result in the standard quantity of counterpart analyte injected. This is defined herein as the 'standard solution'.

It is often helpful to perform an initial study in order to quantify approximately the efficiency with which an analyte may be extracted from any given matrix. To do this a sample of control matrix may spiked with analyte at a concentration such that the approximate efficiency of its extraction from the matrix may be calculated. This may be conveniently achieved using liquid scintillation counting (LSC) for example.

For example, 3,000 dpm of $^{14}$C-labelled analyte can be spiked into 1.5 ml of a control matrix and three 200 µl aliquots are taken for LSC analysis, i.e. with no extraction step having been effected. Another three 200 µl can then be extracted, dried and reconstituted in 200 µl of an appropriate solvent (for example acetonitrile) and the 200 µl aliquots analysed by LSC. If recovery was 100%, then the 200 µl aliquots for the LSC analysis will each contain 400 dpm for which the count time (assuming the count is within the 95.5% confidence interval) is 25 minutes. (The count time T is calculated from $T=1/dpm(200/2)^2$ (assuming the count is within the 95.5% confidence interval).

As noted these preliminary stages are not part of the methods of the invention and it is important to appreciate that, with regard to determination of the approximate extraction efficiency just described, it is not necessary to achieve an extraction efficiency close to 100%. Indeed, the invention arises out of the recognition that this is often not the case. The purpose of the preliminary stage here is to ensure that sufficient amounts of analyte may actually be extracted from the control matrix in order for the method of the invention to work.

Practise of the calibrating method of the invention affords data that may be used to relate the ratio of A:B to absolute values of analyte present. For example, the data may be used to draw a calibration line of A:B against C analogously to that described above for bioanalysis. (It will be understood that each and every reference herein to the ratio A:B could refer instead to B:A, the important point being only that a ratio is obtained).

To obtain such data, from a clinical trial, for example, control matrix (e.g. plasma) is taken, from sources that are uncontaminated with the analyte or counterpart analyte. By uncontaminated is meant that the analyte and counterpart analyte are either absent or are present at undetectable levels. In the context of clinical trials this is conveniently achieved by obtaining control matrix from subjects who have not been exposed to the drug or metabolite under analysis.

To each of a plurality of such control matrix samples, a different concentration of the analyte is added. In addition, an exactly known and equal amount of internal standard (i.e. counterpart analyte) is added to each control matrix sample. After addition of analyte and counterpart analyte, each sample prepared is purified. This will generally involve an initial extraction step, as is known in the art.

It is possible when preparing the plurality of control matrix samples comprising analyte and counterpart analyte for the analyte to be added to the matrix and the quantity of analyte C added to each such control matrix sample determined by AMS analysis of the individual control matrix samples. Where the AMS isotope is $^{14}$C, however, this approach can be problematic since the matrix (e.g. plasma) contains background $^{14}$C. For example, blood contains around 12% w/v carbon, plasma around 4% and urine around 1%. The presence of relatively high concentrations of carbon means that there is endogenous $^{14}$C, which may be regarded as "noise" that affects the Limit of Detection (LOD).

In practice, the LOD for AMS, as with any other analytical technique, is defined by the signal to noise ratio. The signal here depends upon the amount of $^{14}$C from $^{14}$C-enriched analyte. The ratio of $^{14}$C:$^{12}$C is in equilibrium with the ratio of these isotopes present in the atmosphere and is thus fixed for all living entities. Accordingly, the amount of endogenous $^{14}$C increases proportionately with the total amount of carbon in a sample. Thus the LOD for a faeces sample is higher than for a serum sample, since faeces has a higher carbon endogenous carbon content than serum.

As is known in the art, there are ways in which the amount of endogenous carbon in a sample may be reduced, without lowering the quantity of $^{14}$C from the analyte. For example, carbon-rich proteins may be precipitated with water-miscible organic solvents such as acetonitrile, and then removed by centrifugation. A pre-AMS solvent extraction step can likewise lower the amount of endogenous $^{14}$C in faeces.

Because of the presence of endogenous $^{14}$C in biological samples, if control matrix were spiked directly, for example, it has been derived that it is only possible to confirm $^{14}$C concentration down to approximately 0.06 dpm/mL (Lappin, G. & Garner, R. C., infra). In contrast, on HPLC the levels can be lower as there is virtually no $^{14}$C-background.

To address this potential problem, it is preferred for the analyte (and generally, for convenience, the counterpart analyte) to be added (spiked) into the calibrating extraction solvent when preparing the plurality of control matrix samples comprising $^{14}$C-labelled analyte and counterpart analyte, and to analyse by AMS the analyte present in the calibrating extraction solvent to obtain quantity C, since the calibrating extraction solvent contains virtually no non-volatile $^{14}$C-background. (The acetonitrile is removed when preparing the AMS sample). In this way it is possible to construct a calibration curve down to (lower) concentrations more relevant to the test samples that it may be desired to analyse.

In this way, a series of calibrating extraction solvents are prepared, each optionally (but usually) containing the same amount of counterpart analyte (usually at a concentration such that the standard quantity may be injected onto the HPLC) plus varying concentrations of $^{14}$C-analyte. Multiples of the same extraction solvent may be used, which improves the precision of the method. Typically 5 calibrating extraction solvents are used (resulting in typically 0.005 to 2 dpm injected on the HPLC column) but the precise number and concentrations used will depend upon the specifics of the study.

Aliquots of the calibrating extraction solvents (or analyte- and counterpart analyte-spiked control matrices, as appropriate) are taken for AMS analysis, generally at least in duplicate. The results define the precise concentration of $^{14}$C or other AMS isotope added to the control matrix samples.

A stock solution of the counterpart analyte may also be prepared, from which the calibrating extraction solvent(s) is or are made. The same stock solution is typically used to make the standard extraction solvent described below. In this way the calibration curve is constructed using the internal standard at the same concentration as that used for analysis of the test samples.

Control matrix is extracted using the calibrating extraction solvents, typically in duplicate. The final extracts (after drying and reconstitution, if appropriate) are then separated from other components in the sample. Typically this is achieved by HPLC, and the eluates from the HPLC collected as a series of fractions. The fractions corresponding to the retention time of the analyte (and the structurally identical internal standard) are pooled and analysed as a single sample for $^{14}$C, or other AMS isotope, content by AMS. Individual fractions for selected samples may also be analysed to ensure the fraction pool is representative of the analyte.

Separately, another method of sample quantification, typically UV detection, is used to determine the quantity of counterpart analyte.

The data obtained from the calibrating method, i.e. a set of C, A and B values for each of the plurality of purified samples, allows a relationship to be established between the ratio A:B and C. C corresponds to the quantity of analyte added to each of the test samples; A corresponds to the quantity of analyte present in the purified test sample (and would be 100% of C were the extraction (and purification) efficiency 100%); and B corresponds to the quantity of counterpart analyte present in the purified test sample.

It will be appreciated that in the calibratory method of the invention, the data obtained in respect of the AMS isotope assumes that the AMS measurements are of the analyte of interest only. This may not necessarily be the case, however, where the standard contains AMS-labeled species other than the standard this will therefore interfere in at least the measurement of quantity C. However, in practice this possibility is not problematic because the purity of analyte which may be used in a calibratory method of this invention may be determined by other means. Typically, the purity will be certified by the vendor of the analyte.

Generally the quantification of counterpart analyte will be performed upon a sample comprising both analyte and counterpart analyte since these will normally not have been separated from each other and/or the method used to quantify the counterpart analyte will be unable to distinguish between them. This assumes that the quantity of counterpart analyte is much higher than that of analyte, for example in 50-fold excess or more, generally 100-fold excess or more. It will be appreciated that very little indeed of the analyte will in fact be present in many clinical samples because, for example, of the miniscule amounts of analyte present in lightly labeled human microdoses (vide infra) of the total of the counterpart analyte and analyte present in the purified samples.

However, it is also conceivable that the method used to quantify the counterpart analyte may be able to distinguish between counterpart analyte and analyte. An example of such a method is accurate mass spectrometry.

By plotting the ratio of A:B against C, a calibration line may be obtained. It will thus be appreciated how the counterpart analyte serves as an internal standard: any perturbation (e.g. losses and/or non-detection of it) will be in proportion to those losses and/or non-detection suffered by the analyte itself. Since a ratio of the two is taken, these losses cancel out.

Once a calibration line is constructed for a given analyte/counterpart analyte pair, then test (e.g. clinical) samples may be analysed and the amount of analyte present (if any) determined.

Generally, a standard extraction solvent is prepared. This is extraction solvent (typically based on acetonitrile) containing a known concentration of counterpart analyte such that the standard quantity may be injected onto the HPLC, after extraction. As noted above, it is preferable that the standard extraction solvent comprises the same concentration of counterpart analyte as the calibrating extraction solvent. Generally this is achieved by using the same stock solution to make both the standard and calibrating extraction solvent solutions. In this way the calibration curve is constructed using the internal standard at the same concentration as that used for analysis of the test samples.

Thus, to the test sample a known and exact amount of counterpart analyte is added. This acts as the internal standard and also, advantageously, raises the sum of the concentrations of the analyte and counterpart analyte in the sample for reasons described above. Moreover, the counterpart analyte is typically added in great excess to the probable amount of analyte present, and is typically the same as an amount of counterpart analyte added to each sample in the calibratory method of this invention. This is advantageous in that concentration dependent effects are reduced because the overall amount of analyte and counterpart analyte used in the test sample is (a) great enough to reduce losses during extraction and purification; and (b) where the same total of analyte and counterpart analyte are used in the samples in the calibratory method and the test sample, there can be no concentration effect perturbing the data obtained in respect of the test sample.

After extraction, the extracted test sample is purified, e.g. by HPLC. Fractions representing the analyte and counterpart analyte are analysed by AMS (for analyte) and a separate technique (for counterpart analyte) in an exactly analogous fashion to those values obtained according to the calibrating method of the invention.

The ratio A:B obtained in respect of the purified test sample is calculated allowing the original concentration C present in the untreated test sample to be extrapolated from the standard curve.

Periodically (typically twice per day) a small aliquot of standard counterpart analyte, dissolved in HPLC-mobile phase, may be analysed by HPLC-UV to check the UV response when measuring quantity B. Alternatively, any convenient HPLC calibration may be effected, for example, the manufacturer's proprietary or recommended method. AMS is known to be highly consistent over prolonged periods (and indeed because data are based on isotope ratios, consistent between instruments). If, however, the UV response was to drift, then the A:B ratio would be altered leading to errors in the calculation of counterpart analyte concentration. Typically, a CV of less than or equal to 20% is acceptable.

It is to be appreciated that different concentrations of counterpart analytes may be used when practising the two methods of the invention and indeed when preparing the plurality of samples according to the calibratory method of the invention. Whilst using different concentrations of counterpart analytes is less convenient, primarily because more data manipulation is involved, and may in certain circumstances lead to less reliable results, it is not a requirement that the same concentrations (or amounts) of counterpart analytes be used. For example, if x μg of counterpart analyte was used when constructing the calibration curve, this may be considered to afford a value of "B" during the quantification step (v) carried out on the purified calibrating sample. If 2x μg of counterpart analyte was added to a test sample, this may be considered to afford a value of "2B" during the corresponding quantification step (iv). The A:B ratio would then be, for such a test sample, half what it should be in order to be able to read off the initial concentration of the analyte in the test sample from the calibration graph. However, all that need be done to relate the A:B ratios obtained from such test samples is to multiply these ratios by 2.

It is appreciated, however, that by changing the conditions of the method (by using a different amount of internal standard) the assumption that the calibration curve is valid for the test samples may not necessarily be correct in all cases: in reality the "B" value will not be exactly "2B" and so the concentration of analyte calculated with reference to the calibration curve will not be the absolutely true value. Nevertheless, whilst less preferable, it is not required that the same quantity of internal standard be used when conducting analyses of test samples that may have been used when constructing the calibrating data: the quantity of analyte calculated to have been present in the initial test sample will perhaps be, in certain cases, less precise, having possibly been subject to less internal standardisation.

Similar comments apply mutatis mutandis with regard to the lack of need to use the same amount of counterpart analyte when preparing each of the plurality of samples according to the calibratory method of the invention. Thus if x μg of counterpart analyte is present in one sample and 2x μg of counterpart analyte is present in another sample values of "B" and "2B" may be obtained in step (v). In such a case the "2B" value may be divided by 2 in order to prepare A:B (or B:A) ratios based upon x μg counterpart analyte.

The foregoing discussion illustrates a more general point: viz that the first and second aspects of this invention, as defined herein before, relate to distinct aspects of the present invention. The first aspect provides data of use in a subsequent method for determining the quantity of an analyte in a test sample.

In a preferred embodiment of the second aspect of the invention, all aspects of the separating and contacting steps will be conducted under the same conditions as the corresponding separating step according to the calibrating method of the invention, which means that these conditions resemble as closely as practicable the corresponding steps carried out when practising the first aspect of the invention. Similarly, the measuring steps are likewise preferably conducted under the same conditions as the corresponding measuring steps according to the calibrating method of the invention. In this way, the data obtained according to practice of the first aspect of this invention are obtained under the same conditions, or as similar conditions as are practicable, as practised according to the second aspect of the invention. Accordingly, the data obtained in the first aspect of the invention allows quantification of the analyte from the data obtained from practising the second aspect of the invention. The latter data may be correlated with confidence with the former, because both data are obtained under as similar conditions as is practicable. For example, if the extraction method as part of the separating step according to the second aspect of the invention is likely to involve a drying step, then aliquots should preferably be taken for, e.g., LSC analysis before and after drying to check for possible losses of analyte during the drying step.

The most straightforward way of applying the data obtained from the method of the first aspect of the invention when analysing test samples is the so-called pMC method. An alternative approach is the so-called dpm method. Both are explained below with reference to methods in which the AMS isotope is $^{14}C$.

All living entities contain $^{14}C$ in equilibrium with the natural abundance in the atmosphere. A level of $^{14}C$ arbitrarily referred to, or defined, as "100% modern" or 100 pMC, corresponds to one $^{14}C$ atom per $1.18 \times 10^{12}$ atoms of carbon, or 97.6 attamoles of $^{14}C$ per milligram of carbon. AMS standards with precisely known pMC values are available as instrument checks and to normalize data if desired. The two most widely $^{14}C$ standards used are standard oxalic acid from the US National Institute of Standards Technology (NIST) and a crop of sugar harvested in Australia in the 1960s and certified by the Australian National University (ANU). The NIST oxalic acid has a pMC of 95 and ANU sugar a pMC of 150.61 (the latter is >100 because it was harvested during a period when radioactive fallout from atomic weapons was still relatively high).

The "pMC" method allows data processing and calculations to be kept straightforward. However, when using this method a more rigorously standardised approach is preferably taken than when using the dpm method. For example the same experimental protocol is preferably practised in both aspects of the invention.

There is not usually any variation in the matrix extraction methodology and so this will generally not present a difficulty. However, once the sample is injected onto the HPLC, all samples should be treated identically. Specifically:
1. The same number of fractions should be pooled across the analyte HPLC-peak;
2. The same volume should be taken from each fraction to form the fraction pool;
3. The same volume should be aliquoted from the fraction pool for AMS analysis; and
4. The same volume of carbon carrier (e.g. liquid paraffin (LP)) should be added.

With regard to point 4, and as is known in the art, it is conventional in AMS sample preparation to include an amount of material (a carrier material) in which the amount of AMS isotope is essentially negligible, and which material is in great excess to the sample it is wished to analyse by AMS. Typically the weight of the carrier material is present in an amount of 100 to 1,000,000, typically 100 to 10,000 greater than the weight of the purified sample (minus purification solvent, which is removed by evaporation) it is wished to analyse. This is advantageous in two respects:

Firstly it permits, in conventional AMS analysis, analysis of quantities sample (e.g. microgram quantities) that might otherwise be two difficult to handle.

Secondly, with this invention, since excess counterpart analyte is included in the samples and test samples, and as is known by those skilled in the art, these amounts will affect values obtained from the AMS machine because the AMS machine is based upon the calculation of isotope ratios.

In order to calculate the amount of analyte accurately therefore, the amount of an isotope other than the AMS isotope with which the analyte is labeled needs to be known. In practice this is achieved by accurate measurement of the weight of carrier material used. Since the amount of carrier material is in great excess to the sample (as discussed infra) it is reasonable to assume that this constitutes the only source of the non-AMS isotope(s) from which the ratio(s) used to quantify AMS isotope, and so analyte, are obtained.

The carrier material is referred to as carrier and may be any material comprising negligible quantities of the rare isotope under measurement.

If conditions 1 to 4 above are met, then when preparing the standard curve, for example, the pMC value obtained by AMS analysis of the aliquots of the fraction pool can be divided by the UV peak area (the A:B ratio) and plotted on the Y-axis against the C values on the X-axis. For test samples, the pMC value for the analyte peak can be divided by the UV peak area and then correlated from the Y-axis to the X-axis to establish the concentration of analyte in the test sample.

The X-axis could be dpm/mL sample or weight per mL sample. pg or ng/ml is calculated, for example, by dividing dpm/ml by the specific activity of the $^{14}C$-drug administered. The specific activity of the $^{14}C$-analyte used to construct the calibration line is likely to be high (for example around 2 GBq or 50 mCi/mmmol). To calculate the pg or ng values of clinical samples from a standard curve, however, the specific activity of the drug dosed must be used. For example, if a microdose was administered at 100 μg and 200 nCi, then the specific activity will be 2 nCi/μg.

Use of the pMC method removes the need to covert pMC values to dpm values and excludes subsequent routine calculation. For this reason it is the preferable method but it is recognised that analytically this may not be possible, in which case the dpm method described below may be used.

It is perhaps helpful in this context to understand that AMS provides a dpm value per gram of carbon based upon the isotope ratio and not absolute values such as dpm per gram of biological sample. This is a fundamental difference in the output of AMS to LSC. AMS measures the number of $^{14}C$ atoms and not radioactivity decay events. It is only to provide units familiar to biomedical researchers that the isotope ratio is converted into dpm values. To calculate dpm/g of sample values, the proportion of carbon in the sample must be known; this may be readily determined by CHN analysis.

The "dpm" method allows for variation in the analytical methodology but requires more data manipulation. For example, the peak shape may broaden as an HPLC column ages and it may become necessary to pool a larger number of fractions across a peak than was anticipated initially, and that was used to generate the standard curve. Whilst the pMC method is thus preferred, it may be that the practicalities of, e.g. HPLC purification, examples of which are given immediately below mean that the dpm method may be applied.

As noted above, there is not usually any variation in the matrix extraction methods and so this will probably not present a difficulty. Once the sample is injected onto the HPLC, however, it may become necessary to:
(a) pool a different number of fractions across the analyte HPLC peak, compared to that used on the standard curve; and/or
(b) it may be necessary to adjust the pooling regimen and the sample size taken for AMS analysis If conditions (a) or (b) is necessary, then the pMC data should be converted to dpm data. In this process, the fraction volume and aliquot volume are applied to the calculations and so will account for any differences in analytical methodology.

The following examples serve to describe the invention but are not intended to limit it.

Example 1

Construction of a Calibration Curve

Six 1 mL samples of control plasma (human plasma from donors that have never been exposed to the drug being analysed) were taken in separate tubes. Into each tube an amount of $^{14}C$-drug was added to achieve the target concentrations shown in Table 1.

Aliquots were taken from each tube and analysed directly using AMS as described below. The AMS results determined the actual concentrations achieved for each tube as shown in Table 1.

TABLE 1

Radioactive concentrations for the calibration curve.

| Tube | Target concentration (dpm/mL) | Achieved concentration (dpm/mL) |
|---|---|---|
| 1 | 30 | 27.2010 |
| 2 | 8 | 7.8429 |
| 3 | 4 | 3.7710 |
| 4 | 1 | 1.7310 |
| 5 | 0.1 | 0.17310 |

The six plasma samples (200 μL aliquots from each) were then extracted using an exact amount of organic solvent which contained 40 μg/mL non-labelled drug. The extracts were taken to dryness over a stream of nitrogen and reconstituted in 200 μL of solvent.

Aliquots (50 μL) of each of the reconstituted samples were injected onto a HPLC and the HPLC eluate was collected as a series of fractions in 96-well plates. The HPLC was equipped with an UV absorbance detector. The peak area for the HPLC peak corresponding to the drug, as measured by UV absorbance, was recorded.

The retention time of the UV peak was used to locate which fraction in the 96-well plate contained the drug under analysis. This fraction was analysed for $^{14}C$ by AMS.

Following the above analysis the following information was obtained:
1) The actual drug concentration in the plasma samples in dpm/mL as measured directly by AMS (prior to any extraction or HPLC).
2) The concentration of the non-labelled drug in each sample (as an exact and equal amount had been used in the extraction of the plasma samples).
3) Following extraction and HPLC analysis, the UV peak area corresponding to the non-labelled drug for each analysis (note the amount of non-labelled: drug was present in μg amounts. The $^{14}C$-drug was also present but in pg amounts and therefore made an insignificant contribution to the UV peak area).
4) From the AMS analysis, the dpm/mL values for the HPLC fractions.

Calculations

Firstly the results will be calculated not in accordance with this invention, referred to as the conventional method. The conventional method simply takes the concentration of $^{14}C$-drug present in the HPLC fractions (described in the section entitled "Test Sample Measurement" below) and calculates what the concentration should be (dpm/mL) of the initial plasma samples. This conventional method has been reported in the literature on a number of occasions (see R C Garner et al., *Drug Metab Dispos*, 30(7), 823-30. (2002); N Sarapa et al. *J Clin Pharmacol*, 45(10), 1198-205 (2005); J S Vogel, *Biotechniques*, Suppl, 25-9 (2005); and G Lappin et al., *Clin Pharmacol Ther*, 80(3), 203-215 (2006)).

The results of the AMS analysis of the HPLC fractions is shown in Table 2:

TABLE 2

Results of AMS analysis of HPLC fractions

| Tube | dpm per HPLC fraction | dpm/mL plasma* |
|---|---|---|
| 1 | 0.8057 | 16.114 |
| 2 | 0.2241 | 4.482 |
| 3 | 0.1105 | 2.21 |
| 4 | 0.0505 | 1.01 |
| 5 | 0.0050 | 0.1 |

*50 μL from a 200 μL extract was injected onto HPLC, therefore the concentration in the plasma (quoted as dpm/mL) is 20 times that measured in the HPLC fraction.

If the analysis had been 100% efficient (i.e. no losses) then the concentrations reported in Table 2 should be the same as the results of the analysis of the initial plasma samples (i.e. achieved concentration in Table 1). Comparison of the data from Table 1 and Table 2 are shown in Table 3.

TABLE 3

Comparison of results from Tables 1 and 2

| Tube | dpm/mL plasma (from HPLC fractions - from Table 2) | dpm/mL initial plasma (from Table 1) | Percentage difference |
|---|---|---|---|
| 1 | 16.114 | 27.2010 | 59% |
| 2 | 4.482 | 7.8429 | 57% |
| 3 | 2.21 | 3.7710 | 59% |

TABLE 3-continued

Comparison of results from Tables 1 and 2

| Tube | dpm/mL plasma (from HPLC fractions - from Table 2) | dpm/mL initial plasma (from Table 1) | Percentage difference |
|---|---|---|---|
| 4 | 1.01 | 1.7310 | 58% |
| 5 | 0.1 | 0.17310 | 58% |

The results in Table 3 show that there are significant losses during the analysis amounting to approximately 58% for tubes 1-5. The results presented in Table 3 however clearly show that for this analysis, the analytical losses are significant and that the traditional method of sample quantification is seriously in error.

The results will now be recalculated but this time they will be assessed in relation to the internal standard (non-labelled drug) according to the current invention. Results for the peak area for the non-labelled drug are shown in Table 4:

TABLE 4

UV peak areas measured for the internal standard (non-labelled drug).

| Tube | UV peak area |
|---|---|
| 1 | 7969.82 |
| 2 | 8005.14 |
| 3 | 8291.37 |
| 4 | 8203.59 |
| 5 | 7974.84 |

In Table 5, the dpm per fraction is divided by the UV peak area (from Table 4). These ratios are then plotted on the Y-axis of a graph and the actual drug concentration in plasma (achieved concentration (dpm/mL), from Table 1) is plotted on the X-axis (FIG. 1).

TABLE 5

Ratio of dpm/fraction to UV peak area

| Tube | UV peak area | dpm/fraction (from Table 2) | Ratio dpm/mL plasma to peak area |
|---|---|---|---|
| 1 | 7969.82 | 0.8057 | 0.000101098 |
| 2 | 8005.14 | 0.2241 | 0.000021799 |
| 3 | 8291.37 | 0.1105 | 0.000013327 |
| 4 | 8203.59 | 0.0505 | 0.000006156 |
| 5 | 7974.84 | 0.0050 | 0.000000627 |

Example 2

Test Sample Measurement

A plasma sample was prepared so that it contained 6.9498 dpm/mL of drug. The sample was extracted (200 μL) using extraction solvent containing 40 μg/mL non-labelled drug. The extract was taken to dryness and reconstituted in 200 μL solvent and 50 μL was injected onto the HPLC. The peak area for the drug was recorded by UV absorbance. The eluate was collected as a series of fractions and the fraction corresponding to the drug was analysed for $^{14}C$ by AMS. The analysis was conducted twice. Results of the analysis of this sample are shown in Table 6.

TABLE 6 results of the analysis of a test sample

| Duplicate | dpm/ fraction | dpm/mL plasma (conventional method)* | UV peak area | Ratio dpm/mL plasma to peak area | dpm/mL from calibration curve |
|---|---|---|---|---|---|
| 1 | 0.2246 | 4.492 | 8165.82 | 0.0000285049 | 7.43 |
| 2 | 0.2009 | 4.12 | 8156.61 | 0.0000246303 | 6.65 |
| Mean | 0.21275 | 4.306 | 8161.22 | 0.000026567 | 7.04 |

*50 μL from a 200 μL extract was injected onto HPLC, therefore the concentration in the plasma is 20 times that measured in the HPLC fraction.

Analysing the test sample by the direct method (i.e. calculating the plasma concentration directly from the AMS data of the HPLC fractions and not using the calibration curve) gave a mean result of 4.306 dpm/mL. The true value however, was 6.9498 dpm/mL. Thus the result of the HPLC and AMS analysis was 61% low. Analysing the sample using the current invention gave a ratio of dpm/fraction (measured by AMS) to UV peak area of 0.000026567. Taking this value on the Y-axis of the calibration curve (FIG. 1) and correlating this with a concentration on the X-axis gives a mean concentration of 7.04 dpm/mL, which is only 1.3% from true answer.

Analysis of Samples by AMS

The method of graphite production was after Vogel, J. S. (1992) Rapid production of graphite without contamination for biomedical AMS. Radiocarbon, 34 344-350.

Samples of plasma were aliquoted directed (60 μL) into graphitisation tubes. HPLC fractions (typically 100 μL) were aliquoted into graphitisation tubes along with carbon carrier (liquid paraffin, 2.5 μL). The graphitisation tubes were placed in sample tubes containing pre-baked copper oxide wire (50±10 mg) and the whole dried under vacuum using a Savant AES2010 Speed Vac. The final amount of carbon for graphitisation was approximately 2 mg in each case.

Process controls—ANU sugar (a recognised AMS standard for calibration of the AMS instrument; 5-7 mg) and synthetic graphite (2-3 mg) were placed in separate sample tubes containing pre-baked copper oxide wire. 2.5 μL of liquid paraffin control was also placed in separate samples tubes with copper oxide. All standards and controls were dried under vacuum as above.

Combustion (Oxidation)

The glass sample tube containing the dried sample and copper oxide was placed into a larger glass combustion tube, which was heat-sealed under vacuum and heated at 900° C. for two hours in a Carbolite furnace. After combustion, the tubes were allowed to cool slowly to ambient temperature.

Carbon dioxide was produced in the sealed tube by the oxidation of samples and controls during the heating process.

Graphitisation (Reduction)

The pointed end of the larger combustion tube was placed in a Y-manifold. A borosilicate glass tube containing cobalt powder (6.5±1.5 mg) was placed into a larger glass graphitisation tube which contained zinc powder and titanium hydride mix in the ratio of 25:3 w/w (120-200 mg) and the graphitisation tube was attached to the other end of the Y-manifold. The combustion tube was dipped into an isopropanol/dry ice bath and the graphitisation tube into a bath of liquid nitrogen. The whole system was placed under vacuum. Carbon dioxide formed from the oxidised sample was cryogenically transferred to the graphitisation tube after breaking the combustion tube tip. Once transferred, the graphitisation tube was heat-sealed under vacuum and placed in a furnace and heated at 500° C. for four hours, followed by a further six hours heating at 550° C. before slow cooling to ambient temperature.

Packing of Cathodes with Graphite

Once the graphitisation process had been completed, the graphite was left in the sealed graphitisation tube until ready to be packed into a cathode. To pack the cathode, the graphitisation tube was opened and the borosilicate glass tube containing the graphite adsorbed onto the cobalt catalyst removed. The cobalt/graphite was carefully tipped out into an aluminium cathode and compressed into place at 100-200 psi in a Parr Pellet Press to form a tablet of graphite within the cathode. After every pressing, the press was cleaned by wiping it with tissue moistened with methanol. The sample and process control cathodes were then placed into labelled plastic capped tubes for storage at room temperature. When required for analysis, these cathodes were placed into a 134-position AMS sample wheel with the other machine standards and controls shown below.

AMS Standards and Controls used for AMS Analysis

| Standard/control | Purpose | Usual No of cathodes |
|---|---|---|
| Solid aluminium cathode | Machine blank | 1 |
| POCO graphite | $^{14}C$-depleted for instrument tuning | 1 |
| Pooled ANU sugar | Standard normalisation | 3 |
| ANU sugar | Process control | 4 |
| Synthetic graphite[1] | Machine blank | 2 |
| Process graphite | Process control | 2 |
| Liquid Paraffin[2] | Process control | 5 |

[1] mixed with 30% v/v aluminium powder
[2] carrier liquid

The above cathodes were used to either tune the AMS instrument or as a measure of process effectiveness with the exception of pooled ANU sugar cathodes which were used in data normalisation.

AMS Procedure

AMS analysis was performed using a 5 MV 15SDH-2 Pelletron AMS system (National Electrostatics Corporation). The sample wheel in which the graphite-containing cathodes were placed, was inserted into the ion source of the AMS instrument. The multi-cathode negative ion source (MC-SNICS) generated a caesium ($Cs^+$) ion beam that was accelerated onto the graphite surface. The resulting negative carbon ion beam contained $^{12}C^-$, $^{13}C^-$ and $^{14}C^-$ and other ions such as $^{16}O^-$. The isobar $^{14}N^-$ is unstable and therefore cannot interfere with the $^{14}C$ measurement.

The carbon ion beam was pre-accelerated, passed through a spherical electrostatic analyser and then progressed towards the injection magnet. Output of $^{12}C^-$ was typically 1-100 μA. The magnet was set to inject $^{12}C^-$ (150 μs), $^{13}C^-$ (600 μs) and $^{14}C^-$ (0.1 s) ions sequentially at normally 68 keV; one combined measurement on each isotope in turn corresponded to one cycle. The carbon ion beam was accelerated towards the positive centre terminal of the tandem Pelletron accelerator through an Einzel lens. The terminal voltage used for this series of analyses was between 3.5 and 4.5 MV with a particle energy of approximately 17.5 to 22.5 MeV. At the central terminal electrons were stripped from the carbon atom to yield positively charged carbon ions ($^{12,13,14}C^{+1 \; to \; +6}$). $C^{4+}$ ions were selected for measurement as these were the most abundant at this energy. These ions were accelerated away from the centre terminal and onwards towards the electrostatic quadruple triplet and analysing magnet.

Immediately past the post-analysing magnet, $^{12}C^{4+}$ and $^{13}C^{4+}$ ions were measured as an ion current in offset Faraday cups. $^{14}C^{4+}$ Ions were passed down the high energy beam line, through an electrostatic quadrupole doublet and a cylindrical electrostatic analyser. From here, the ions entered a gas ionisation detector where they were collected on anodes (four in total) which measured the energy loss and total energy of each ion. Other interfering non $^{14}C^{4+}$ ions were generally prevented from entering the gas ionisation detector by the combinations of electrostatic analysers, magnets, slits and charge state separation. Vacuum pressures of approximately $10^{-9}$ Torr were maintained in the beam line and $10^{-6}$ Torr in the ion source. Ion transmission through the instrument was between 30-60%.

Treatment of Data

The AMS data was used to calculate the dpm/mL values for the prepared samples. The AMS results were expressed as pMC, where 100 pMC equals:
13.56 dpm/g C or 0.01356 dpm/mg C
or 98 femtomole $^{14}C$/g C (1 femtomole=$10^{-15}$ Mole)
or 98 attomole $^{14}C$/mg C (1 attomole=$10^{-18}$ Mole)
Thus, $$pMC \times 0.1356 = dpm \; ^{14}C/g \; C$$

and $$(dpm \; ^{14}C/g \; C) \times (\% \; w/v \; C \; in \; sample) = dpm \; ^{14}C/mL$$

assuming the density of a sample to be 1 g/$cm^3$

The $[^{14}C]/[^{14}C]$ ratio of a sample =

$$\frac{\text{Total } [^{14}C] \left( \begin{array}{c} \text{drug} + \\ \text{biological sample} + \\ \text{carrier}^1 \end{array} \right)}{\text{Total } [^{12}C] \left( \begin{array}{c} \text{drug} + \\ \text{biological sample} + \\ \text{carrier}^1 \end{array} \right)}$$

1 – Where applicable

Mathematical Treatment

The discussion that follows describes the same concepts of the invention fully described hereinabove, but with a discussion on mathematical codification of the internal standardisation provided for by the present invention. As with the preceding discussion, the discussion below is exemplified with $^{14}$C-labelled compounds although it will be appreciated that the concepts apply equally to other AMS isotope-labelled compounds.

Whilst AMS is being used increasingly for example in the measurement of $^{14}$C-drug concentration in certain study types during drug development, and equations are well-established for the measurement of total drug and metabolites (e.g. $^{14}$C or other AMS isotope concentration) in a biological sample, equations have not been derived to allow for the losses that occur as a result of chromatographic separation of analyte and analysis by AMS. When such equations are derived, it will be appreciated from the discussion hereinabove that any mass loss occurring during analysis has to be taken into account in order to measure accurately the analyte concentration. With the benefit of the present invention, in the light of the methods of the invention relating to accounting for any mass-loss during analysis, equations describing chromatographic separation and AMS analysis of $^{14}$C- and other AMS isotope-containing analytes may be derived.

Being an isotope ratio method, AMS requires the presence of at least two isotopes in the analyte, typically $^{12}$C and $^{14}$C for drug substances. In order to measure the isotope ratio, samples are typically converted to graphite, which is then placed into the AMS for analysis. (J. S. Vogel, *Rapid production of graphite without contamination for biomedical AMS*. Radiocarbon 34 (1992) 344-350). AMS is extremely sensitive, being able to measure $^{14}$C-drug concentrations in the femtogram or attogram range ($10^{-15}$-$10^{-18}$ g), depending upon the specific activity of the $^{14}$C-drug (G. Lappin, and R. C. Garner, *Ultra-sensitive detection of radiolabelled drugs and their metabolites using accelerator mass spectrometry*. in: I. Wilson, (Ed.), *Handbook of Analytical Separations*, Elsevier, Amsterdam, 2003, pp. 331-349). Because of its extreme sensitivity, and as described hereinbefore, AMS has been applied to techniques such as microdosing and absolute bioavailability studies. Since there is no commonly-available interface between HPLC and AMS, plasma extracts are analysed by HPLC and fractions of the HPLC eluant corresponding to the retention time of the analyte of interest are graphitised "off-line" before the $^{12}$C:$^{14}$C isotope ratio is determined (I. N. White, and K. Brown, *Techniques: the application of accelerator mass spectrometry to pharmacology and toxicology*. Trends Pharmacol Sci 25 (2004) 442-7).

Vogel and Love (J. Vogel, and A. H. Love, *Quantitating Isotopic Molecular Labels with Accelerator Mass Spectrometry*. in: A. L. Burlingame, (Ed.), *Methods in Enzymology*, Academic Press, New York, 2005) have described how an isotope ratio measured for a biological sample is converted to a drug concentration, which may be represented by equation 1:

$$K=(R_M-R_N)\cdot\Psi\cdot W/L \qquad \text{(equation 1)}$$

where K is the concentration of analyte, $R_M$ is the isotope ratio, $R_N$ is the natural background isotope ratio of the biological sample, $\Psi$ is the carbon mass fraction in the sample, W is the molecular weight of the analyte and L is the specific molar activity of the analyte.

The isotope ratio is expressed by AMS in units of Modern, where 1 Modern=98 attomole $^{14}$C/mg carbon. Because the isotope ratio is expressed relative to the mass of carbon, then the mass fraction ($\Psi$) in the sample is included in the equation to convert a concentration per mass of carbon to per mass of sample. The mass fraction is measured with a routine carbon analyser.

Equation 1 can be simplified whereby $(R_M-R_N)$ is expressed as $R_{net}$ and the specific activity is expressed relative to mass ($L_{mass}$) instead of moles, giving equation 2:

$$K = \frac{R_{net}\Psi}{L_{mass}} \qquad \text{(equation 2)}$$

Equations 1 and 2 are generally well-established but, where a drug has been metabolised, then the results of the equations only provide the total $^{14}$C (referring hereafter to $^{14}$C as an example) for the mixture of parent drug and metabolites (i.e. mass equivalents). To determine the concentrations of the individual analytes present, and as described hereinbefore, the sample has typically to be extracted and analytes separated by a chromatographic technique, such as HPLC, prior to AMS analysis. So far, equations that describe this process have not been reported and, with the benefit of the present invention, are derived here for the first time.

Assuming that the analyte was separated from any background carbon following HPLC, then $R_N=0$. Thus to distinguish $R_{net}$ from the isotope ratio of the separated analyte, the latter is designated $R_A$. The specific activity of the drug as administered to laboratory animals or humans ($L_{mass}$) is unchanged by biochemical processes and therefore the specific activity of the analyte isolated by HPLC must be equal to that of the parent drug (i.e. $R_A$=L). Substituting in equation 2, $K=\Psi$, in other words the amount of analyte in the HPLC fraction is equal to the amount of carbon from the analyte in the fraction, which is essentially the same thing. It may appear, therefore, that the concentration of the isolated analyte cannot be determined from its isotope ratio. It is possible to overcome this limitation, however, as described hereinbefore, by performing an isotope dilution by the addition of $^{12}$C, but not $^{14}$C to the isolated analyte. Such isotope dilutors (referred to hereinabove as carrier materials) are available as carbon from petrochemical sources that are immensely old and therefore the $^{14}$C has decayed away ($t_{1/2}$ $^{14}$C=5760 years=173 half-lives per $10^6$ years). A typical isotope dilutor of this type is liquid paraffin. The use of liquid paraffin in AMS analysis is well established, the liquid paraffin carrier material being referred to as a "carbon carrier", since it is mainly used to bulk up very small samples to a manageable size (G. Lappin, and S. Temple, *Accelerator Mass Spectometry in: Radiotracers in Drug Development*, Taylor and Francis CRC Press, Florida, USA, 2006). In the case of fractions isolated by HPLC, however, and again as noted hereinabove, the carbon carrier serves an addition purpose of isotope dilution.

Let the $^{14}$C:$^{12}$C ratio in the analyte purified from the sample by chromatography=$R_A$ (as above). Let the amount of $^{12}$C added to $R_A$ for isotopic dilution (i.e. the amount of $^{12}$C in the carbon carrier)=$\phi$. Let the resultant $^{14}$C:$^{12}$C ratio after isotopic dilution=$R_D$. By substituting in equation 2, gives equation 3:

$$K = \frac{R_D\phi}{L_{mass}}. \qquad \text{(equation 3)}$$

Equation 3 indicates that it is preferred that the isotope dilution be accurately known: any error will translate directly to an error in the final result. The amount of carbon carrier can be accurately dispensed and hence is known, but any analytical losses of the analyte, for example in extraction or on the HPLC column, will also lead to errors in the determination of K. Another parameter representing the analytical recovery (θ) may be thus be introduced into equation 3 to afford equation 4:

$$K = \frac{R_D \phi}{L_{mass} \theta} \quad \text{(equation 4)}$$

Whilst it is possible to measure θ by simply conducting experiments to determine a generic experimental recovery, and this may be acceptable in cases where it can be shown that the recovery is reproducible, it is more desirable to measure the recovery individually for each sample analysed. As explained hereinbefore, this can be achieved in a manner similar to that routinely used in quantitative HPLC analysis, with the use of an internal standard. It is generally impractical to use a $^{14}$C-labelled internal standard since these compounds have limited availability and are often relatively expensive to manufacture. Instead however, it is possible to use non-radiolabelled analyte (the counterpart analyte) as the internal standard and measure the concentration in each sample by a routine detection method such as UV absorbance.

The addition of counterpart analyte to the sample does not interfere with the measurement the analyte since it is distinguished by the presence of the AMS isotope, typically $^{14}$C. The small amount of $^{12}$C added to the sample from the counterpart analyte is insignificant compared to the $^{12}$C in the carbon carrier (as noted above, and known to those in the art, typically μg amounts of counterpart analyte are added and mg amounts of carbon carrier are used). In addition, where the counterpart analyte is added as a constantly, equal and exactly known amount (this is typical but not required) then all the samples in effect contain the same total concentration of analyte and there are therefore minimal concentration-dependant effects. This is advantageous bearing in mind that, with AMS analysis, the concentration of the analyte in a sample is often very small and losses due to non-specific binding can be significant. The addition of excess counterpart analyte helps overcome these non-specific binding effects thereby improving recovery.

As described above the procedure for using counterpart analyte as an internal standard follows a procedure analogous to that employed in HPLC analysis. A standard curve may be first generated whereby a series of plasma samples are spiked with rising concentrations of $^{14}$C- or other AMS isotope-labelled drug along with a known and generally equal amount of counterpart analyte as an internal standard. The "true" concentration of $^{14}$C- or other AMS isotope-labelled drug in each spiked calibrant is determined from the amount accurately dispensed. In addition, because the total $^{14}$C concentration equals the concentration of the $^{14}$C-drug under these circumstances aliquots of the calibrants can be analysed directly with AMS (equation 2) to obtain an actual measurement (quantity "C" as hereinbefore defined). Each plasma sample is extracted, the extract run on HPLC and the fraction corresponding to the retention time of the analyte is collected, (typically) graphitised and the $^{12}$C:$^{14}$C ratio (typically expressed as Modern) measured by AMS. In addition the UV response for the counterpart analyte peak (internal standard) is measured (as noted above UV is used as an example but any suitable measurement technique could be used). The standard curve is then constructed from the true concentration ("C") on the X-axis and the Modern value for the HPLC fraction ("B") divided by its UV response ("A") on the Y-axis. AMS provides a linear response up to the point where the $^{14}$C-detector becomes saturated. Since saturation can damage the detector, this is avoided and so in practice the response is always linear (L. K. Fifield, *Accelerator Mass spectrometry and its applications. Rep Prog Phys* 62 (1999) 1223-1274). A line may therefore be fitted to the calibration data by linear regression. It is important to understand that the standard curve described here differs from the usual HPLC calibration line in that it does not calibrate an instrument response. As is known to those in the art, AMS instruments may be calibrated $^{12}$C:$^{14}$C ratios such as using separate standards with precise Australian National University sugar or oxalic acid (G. Lappin, and S. Temple, *Accelerator Mass Spectrometry in: Radiotracers in Drug Development*, Taylor and Francis CRC Press, Florida, USA, 2006).

To each sample under analysis, a known (normally the same as that used in the calibratory method described above) amount of counterpart analyte is added as an internal standard. The sample is extracted, run on HPLC and the fraction corresponding to the retention time of the analyte is collected, graphitised and the Modern value determined by AMS. In the same way as described for the standard curve, the UV response is also measured. The Modern value for the fraction divided by its UV response on the Y-axis then determines the drug concentration from the corresponding value on the X-axis. Since the correspondence between the Y and X axis defines the slope of the curve (and being linear, its equation is y=mx+c), then substituting in equation 3, gives equation 5:

$$K = \frac{\left(\frac{R_A}{mU} + C\right)\phi}{L_{mass}} \quad \text{(equation 5)}$$

where K is the amount of the analyte in the HPLC fraction, $R_A$ is the Modern value of the analyte after isotope dilution, φ is the amount of $^{12}$C added as the isotope dilutor, $L_{mass}$ is the mass specific activity of the analyte, m is the slope of the standard curve, U is the UV response (or detector response of any suitable detection method) and C is the intersect of the standard curve on the Y axis.

Figure 2:
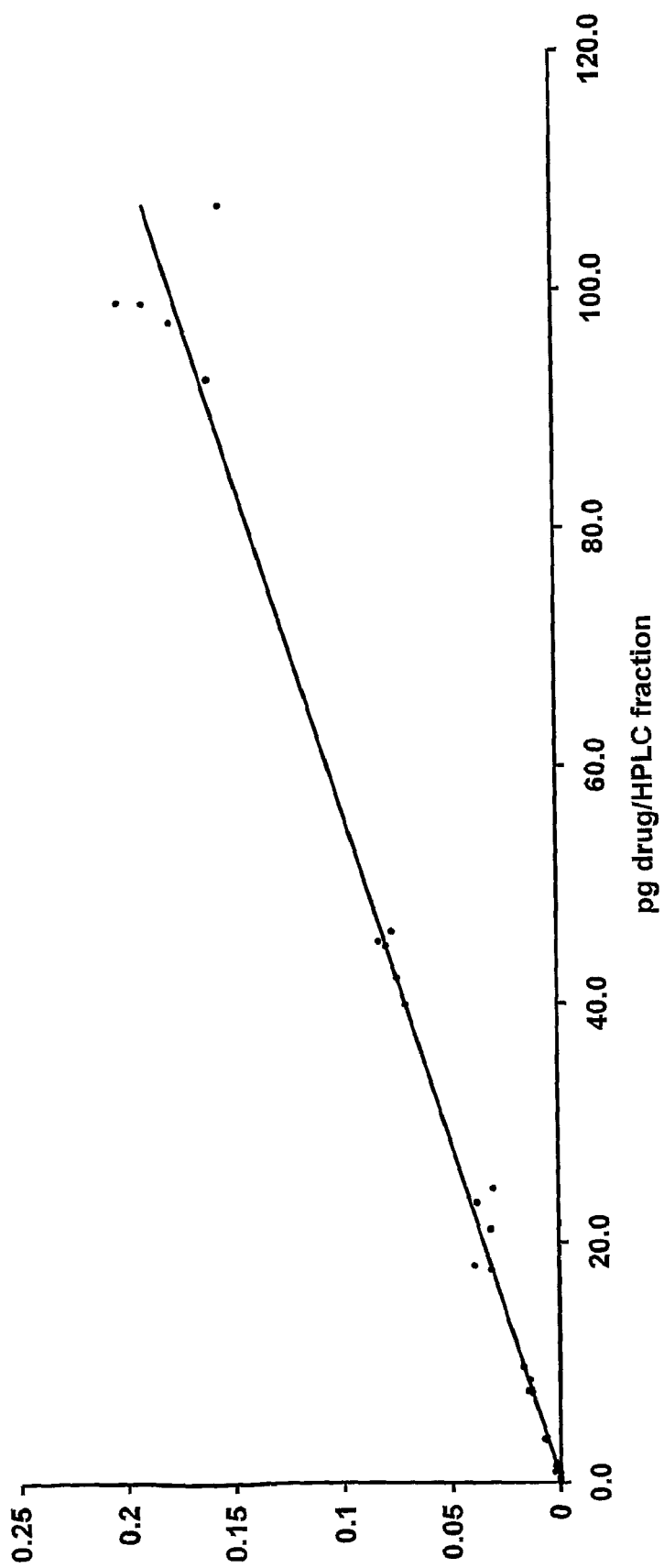
FIG. 2 shows a further calibration curve obtained by plotting a ratio of B:A against C for data obtained from practice of a calibratory method of the invention.

A typical standard curve, constructed as described above, is shown in FIG. 2. FIG. 2 shows a further calibration curve obtained by plotting B:A ratios against C values for 7 different concentrations of a $^{14}$C-labelled drug each consisting of 5 separate replicates. In this particular standard curve 7 concentrations of $^{14}$C-drug were used each consisting of 5 separate replicates. Liquid paraffin was used as the carbon carrier (1.6266 mg $^{12}$C). The concentration of non-radiolabelled analyte as the internal standard was 35 μg/mL. The slope of the line was 0.1359 and the value for c was −0.0866. In practice the value for c is often negligible and can be ignored. The range for the standard curve shown in FIG. 2 was 1 fg to 160 pg/HPLC fraction.

Plasma spiked with $^{14}$C-drug and accurately diluted to achieve an equivalent range of 4 fg to 120 pg/HPLC fraction was extracted and analysed by HPLC and AMS. The concentrations as determined from the standard curve, were on average 97.2% (n=25) of the true value (range 84.2-118.8%). Without the standard curve and without accounting for analytical losses (i.e. equation 3), the concentrations of the spiked plasma samples were determined as an average of 69.1% of the true value (n=25) ranging from 52.8-92.3%. Thus the average analytical recovery was approximately 72%. Without taking any recovery into account therefore (i.e. assuming θ in equation 4 to be 1) the results showed an average error of −28%. This error was reduced to an average of 2.8% using the internal standard method described according to the present invention.

The invention claimed is:

1. A calibrating method for use determining the quantity of an analyte labeled with an accelerator mass spectrometry isotope in a test sample, said calibrating method comprising:
   (i) contacting a plurality of samples contaminated with neither said analyte nor a non-labeled counterpart analyte with a known quantity of said counterpart analyte and a quantity C of said analyte to afford a plurality of calibrating samples, wherein each of said calibrating samples contains a known quantity of said counterpart analyte and a different quantity C of said analyte;
   (ii) measuring by accelerator mass spectrometry the quantity C of said analyte added to each of the plurality of samples;
   (iii) separating said analyte and said counterpart analyte from other species in the plurality of samples to afford a plurality of purified samples;
   (iv) measuring a quantity A of said analyte in said purified samples by accelerator mass spectrometry; and
   (v) measuring a quantity B of said counterpart analyte in said purified samples; and relating the measured quantities C to ratios of measured quantities A and B for each of the plurality of samples to allow for determination of the quantity of said analyte in said test sample.

2. The calibrating method of claim 1 wherein the same quantity of counterpart analyte is added to each of said plurality of said calibrating samples.

3. The calibrating method of claim 1 wherein said measuring of quantity C is conducted before contact of the counterpart analyte with each of said samples.

4. The calibrating method of claim 1 wherein the samples are of human or animal origin.

5. The calibrating method of claim 1 wherein the samples are of human origin.

6. The calibrating method claim 1 wherein the samples are of urine, faeces, plasma or blood.

7. The calibrating method of claim 6 wherein the samples are of blood.

8. The calibrating method of claim 6 wherein the samples are of plasma.

9. The method of claim 1 wherein the accelerator mass spectrometry isotope is selected from the group consisting of $^3$H, $^7$Be, $^{10}$Be, $^{14}$C, $^{17}$O, $^{18}$O, $^{26}$Mg, $^{26}$Al, $^{32}$Si, $^{35}$S, $^{36}$Cl, $^{41}$Ca, $^{55}$Fe, $^{60}$Fe, $^{53}$Mn, $^{79}$Se, $^{59}$Ni, and $^{129}$I.

10. The method of claim 9 wherein the accelerator mass spectrometry isotope is selected from the group consisting of $^3$H and $^{14}$C.

11. The method of claim 10 wherein the accelerator mass spectrometry isotope is $^{14}$C.

12. The method of claim 1 wherein the analyte is a drug candidate.

13. The method of claim 1 wherein the analyte is a metabolite of a drug candidate.

14. The method of claim 1 wherein the separating comprises separating by HPLC.

15. The calibrating method of claim 1 wherein the measuring of quantity B is achieved by measuring UV absorption of counterpart analyte.

16. A quantitative method for determining the quantity of an analyte labeled with an accelerator mass spectrometry isotope in a test sample, said method comprising:
   (i) contacting said test sample with a known quantity of a non-labeled counterpart analyte;
   (ii) separating said analyte, if present, and said counterpart analyte from other species in the test sample to afford a purified test sample;
   (iii) measuring a quantity A of said analyte in said purified test sample by accelerator mass spectrometry;
   (iv) measuring a quantity B of said counterpart analyte in said purified test sample; and
   (v) determining the quantity of analyte present is said test sample;
       wherein said quantitative method further comprises a calibrating method comprising:
   (a) contacting a plurality of samples contaminated with neither an analyte labeled with an accelerator mass spectrometry isotope nor a non-labeled counterpart analyte with a known quantity of said counterpart analyte and a quantity C of said analyte to afford a plurality of calibrating samples, wherein each of said calibrating samples contains a known quantity of said counterpart analyte and a different quantity C of said analyte;
   (b) measuring by accelerator mass spectrometry the quantity C of analyte added to each of the plurality of samples;
   (c) separating said analyte and said counterpart analyte from other species in the plurality of samples to afford a plurality of purified samples;
   (d) measuring a quantity A of said analyte in said purified samples by accelerator mass spectrometry; and
   (e) measuring a quantity B of said counterpart analyte in said purified samples;
       wherein the same analyte and counterpart analyte are employed in both the quantitative method and the calibrating method; and
   relating the measured quantities C to ratios of measured quantities A and B for each of the plurality of calibrating samples to allow for determination of the quantity of said analyte in said test sample.

17. The method of claim 16 wherein the test sample is of human or animal origin.

18. The method of claim 17 wherein the test sample is obtained from a subject previously administered with a microdose of analyte and counterpart analyte.

19. The method of claim 17 wherein the test sample is of urine, faeces, plasma or blood.

20. The method of claim 19 wherein the test sample is of blood.

21. The method of claim 19 wherein the test sample is of plasma.

22. The method of claim 16 wherein the test sample is of human origin.

23. The method of claim 16 wherein the test sample is contacted with the same quantity of counterpart analyte as the calibrating samples in the calibrating method.

24. The method of claim 16 wherein the contacting, separating and measuring steps (i)-(iv) of the quantitative method are conducted under the same conditions as the contacting, separating and measuring steps (a) and (c)-(e) of the calibrating method.

* * * * *